US009629993B2

(12) United States Patent
Klewinghaus (10) Patent No.: US 9,629,993 B2
(45) Date of Patent: Apr. 25, 2017

(54) TUBING ADAPTER FOR INFLUENCING THE PRESSURE INSIDE A TUBING SECTION DURING A MEDICAL TREATMENT

(71) Applicant: Fresenius Medical Care Deutschland GmbH, Bad Homburg OT (DE)

(72) Inventor: Juergen Klewinghaus, Oberursel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/792,389

(22) Filed: Mar. 11, 2013

(65) Prior Publication Data

US 2013/0237903 A1 Sep. 12, 2013

Related U.S. Application Data

(60) Provisional application No. 61/609,387, filed on Mar. 12, 2012.

(30) Foreign Application Priority Data

Mar. 12, 2012 (DE) .................. 10 2012 004 673

(51) Int. Cl.
| | | |
|---|---|---|
| A61M 25/16 | (2006.01) | |
| A61M 25/18 | (2006.01) | |
| A61M 39/00 | (2006.01) | |
| A61M 39/10 | (2006.01) | |
| A61M 39/22 | (2006.01) | |
| A61M 39/24 | (2006.01) | |
| A61M 5/168 | (2006.01) | |
| A61M 1/16 | (2006.01) | |

(52) U.S. Cl.
CPC ............ *A61M 39/10* (2013.01); *A61M 1/166* (2014.02); *A61M 5/16813* (2013.01); *A61M 39/22* (2013.01); *A61M 39/24* (2013.01); *A61M 2039/242* (2013.01); *A61M 2039/2413* (2013.01); *F04C 2270/0421* (2013.01)

(58) Field of Classification Search
CPC .......... A61M 1/166; A61M 2039/2413; A61M 2039/242; A61M 39/22; A61M 5/16813
USPC .............................. 604/28–34, 533–534, 537
See application file for complete search history.

(56) References Cited

U.S. PATENT DOCUMENTS

| | | | |
|---|---|---|---|
| 5,863,421 A | 1/1999 | Peter, Jr. et al. | |
| 6,044,859 A * | 4/2000 | Davis .................... | 137/15.19 |
| 2003/0216712 A1 | 11/2003 | Kessler et al. | |
| 2005/0020959 A1 | 1/2005 | Brugger | |
| 2009/0008306 A1* | 1/2009 | Cicchello et al. ........ | 210/85 |
| 2009/0010627 A1 | 1/2009 | Lindsay et al. | |

(Continued)

FOREIGN PATENT DOCUMENTS

| | | |
|---|---|---|
| DE | 4313636 C1 | 10/1994 |
| DE | 19605260 A1 | 11/1996 |
| DE | 19650664 C1 | 1/1998 |

(Continued)

*Primary Examiner* — Rebecca E Eisenberg
(74) *Attorney, Agent, or Firm* — Fish & Richardson P.C.

(57) ABSTRACT

A tubing adapter for interconnection with a least one tubing section of a medical device, a dialysis fluid tubing system including such a tubing adapter, a medical device including such a dialysis fluid tubing system, and a method for avoiding a pressure within a dialysis fluid tubing system that is below a minimum pressure are described.

19 Claims, 3 Drawing Sheets

(56) References Cited

U.S. PATENT DOCUMENTS

2011/0315611 A1    12/2011   Fulkerson et al.

FOREIGN PATENT DOCUMENTS

| | | |
|---|---|---|
| DE | 69131203 T2 | 9/1999 |
| DE | 10055283 A1 | 6/2002 |
| DE | 10319197 B3 | 7/2004 |
| DE | 102007018362 A1 | 10/2008 |
| WO | 9605883 A1 | 2/1996 |
| WO | 9625214 A1 | 8/1996 |
| WO | 98-39589 A1 | 9/1998 |
| WO | 0057935 A1 | 10/2000 |
| WO | 01-91829 A2 | 12/2001 |

\* cited by examiner

TUBING ADAPTER FOR INFLUENCING THE PRESSURE INSIDE A TUBING SECTION DURING A MEDICAL TREATMENT

CROSS REFERENCE TO RELATED APPLICATIONS

The present application claims priority to U.S. Provisional Application Ser. No. 61/609,387, filed on Mar. 12, 2012, and Application No. DE 10 2012 004 673.1, filed in the Federal Republic of Germany on Mar. 12, 2012, each of which is expressly incorporated herein in its entirety by reference thereto.

FIELD OF INVENTION

The present invention relates to a tubing adapter, a dialysis fluid tubing system and a medical device. Moreover, the present invention relates to a method for using a tubing adapter according to the present invention and a method for avoiding the occurrence of a pressure within the dialysis fluid tubing system below a minimum pressure.

BACKGROUND INFORMATION

From treating patients by dialysis devices, it is known to heat dialysis fluid before the fluid flows into the dialyzer or blood treatment filter in which substances, e.g., blood and dialysis solutions, are exchanged through a membrane which usually is of a semi-permeable type. Some of these heating devices require achieving a secure contact or require keeping a maximum distance between the heating device, which may for example be shaped as heating coils or heating spindles, and a container containing the dialysis fluid to be heated, in which the container is surrounded by said heating device and the container may by way of example be embodied as a bag. With a heating device of this type, heating the dialysis fluid as intended depends on how well the container contacts the heating device, which may, for example, be embodied as a bag heater (or vice versa).

SUMMARY

An object of the present invention is to propose devices and methods for achieving or ensuring a desired or required contact between the heating device and the container comprising dialysis fluid, or for avoiding that the distance between the heating device and the container during use or while the patient is being treated exceeds a maximum value.

An object according to the present invention is solved by a tubing adapter, a dialysis fluid tubing system and by a medical device. Moreover, an object of the present invention is solved by a method for using a tubing adapter and by a method for avoiding the occurrence of a pressure within the dialysis fluid tubing system below a minimum pressure.

Hence, according to the present invention a tubing adapter for connecting with at least one tubing section of a dialysis fluid tubing system is proposed. Alternatively, the tubing adapter according to the present invention may be inserted between two tubing sections of a dialysis fluid tubing system or may be intended to be used and adapted accordingly. Both the tubing adapter and the tubing section are intended and embodied to be perfused by the dialysis fluid when being used as intended.

The tubing adapter according to the present invention comprises at least one locking mechanism for temporarily or reversibly blocking a flow-through lumen of the tubing adapter or of the tubing section connected thereto, and a device for generating or amending a flow resistance, or both.

The dialysis fluid tubing system according to the present invention comprises at least one tubing adapter according to the present invention or is integral with (or is an integral part of) such one tubing adapter or comprises at least one locking mechanism for blocking its flow-through lumen or a device for generating or amending of the flow resistance, or both.

The medical device according the present invention comprises at least one dialysis fluid tubing system according to the present invention or is connected thereto.

Using the tubing adapter according to the present invention in accordance with the present invention encompasses interconnecting the tubing adapter with a dialysis fluid tubing system, in particular with one or more dialyzer couplings of the dialysis fluid tubing system, the couplings being embodied for interconnecting the dialysis fluid tubing system with the dialyzer or blood filter.

Further, according to the present invention a method is suggested for avoiding a pressure within the dialysis fluid tubing system that is below a minimum pressure. The method encompasses interconnecting a tubing adapter according to the present invention with the dialysis fluid tubing system or it encompasses arranging of a locking mechanism for blocking a flow-through lumen of the dialysis tubing system or it encompasses arranging a device for generating or amending a flow resistance within the dialysis fluid tubing system, or both. The interconnecting or arranging takes place downstream of a heating device which is interconnected to dialysis fluid tubing system.

In the following, "can/may be" or "can/may have" and so forth may be understood as "preferably is" or "preferably has" and so forth and is to be understood as being related to an exemplary embodiment according to the present invention.

Exemplary embodiments according to the present invention may have one or several of the features stated as follows.

In some exemplary embodiments according to the present invention, the flow resistance changes step-wisely or not steadily, or both.

In certain exemplary embodiments according to the present invention the tubing adapter is in fluid communication with the tubing adapter of the dialysis fluid tubing system with which it is interconnected. Therefore, when being used, the tubing section is being flown-through by the same fluid or by the same amount of fluid, or both, as the tubing section.

In some exemplary embodiments according to the present invention, the flow resistance is generated or amended, or both, by the tubing adapter or by one of its components.

In certain exemplary embodiments according to the present invention the tubing adapter is intended and embodied or both to be interconnected with at least one tubing section of the dialysis fluid tubing system for being used.

In some exemplary embodiments according to the present invention, the change of the flow resistance takes place within the flow-through lumen of the tubing adapter according to the present invention.

In particular exemplary embodiments according to the present invention, the flow resistance is changed according to a pressure drop or causes one.

In some exemplary embodiments according to the present invention, a flow through the tubing adapter is blocked by the locking mechanism in its blocked state.

In certain exemplary embodiments according to the present invention, an entry of dialysis fluid from a source of dialysis fluid into the dialyzer is blocked by the locking mechanism in its blocked state.

In some exemplary embodiments according to the present invention, a flow through the tubing adapter is impeded by the locking mechanism depending on a pressure upstream of the tubing adapter according to the present invention, in particularly downstream of a heating device, for example embodied as a bag heater, by which the dialysis fluid guided through the tubing adapter was heated.

In certain exemplary embodiments according to the present invention, a flow, or any flow, downstream of the tubing adapter and upstream of the tubing adapter is amended or impeded by the device for generating a flow resistance during normal use of the tubing adapter depending on a pressure upstream of the tubing adapter according to the present invention.

In some exemplary embodiments according to the present invention, the locking mechanism and the device for generating a flow resistance, or both, serve to rule out or exclude pre-defined pressures upstream of the tubing adapter. A pre-defined pressure may be a vacuum or negative pressure or a pressure below a pre-defined minimum pressure.

The pre-defined minimum pressure may be defined or set by selecting the particular elements such as a non-return valve or a pressure stop valve.

The terms non-return valve and pressure stop valve are being used interchangeably in some exemplary embodiments according to the present invention whenever this is considered by the skilled person as possible from a technical point of view.

In some exemplary embodiments according to the present invention the minimum pressure is a vacuum or a negative pressure. In certain exemplary embodiments according to the present invention the minimum pressure is a pressure at which a container or a bag of the actually used bag heater does reliably not collapse if this pressure is applied inside of the container or bag. In some exemplary embodiments according to the present invention the minimum pressure or the pressure difference is 0 hPa each.

In certain exemplary embodiments according to the present invention the minimum pressure relates to a pressure inside of the container or bag of the bag heater actually used; in other exemplary embodiments according to the present invention the minimum pressure relates to a pressure inside of the dialysis fluid tubing system between the heating device and dialyzer.

In some exemplary embodiments according to the present invention the tubing adapter or components thereof are located upstream of the inlet of the dialyser for dialysis liquid.

In certain exemplary embodiments according to the present invention the fluid entering the tubing adapter or components thereof is the same fluid flowing out from there. A processing of the fluid or a manipulation of its composition does not take place within the tubing adapter in those exemplary embodiments according to the present invention. No infusions or the like are added within the tubing adapter in those exemplary embodiments. The tubing adapter is not adapted or intended for that. The tubing adapter is not a port valve or a multi-port-valve, in some exemplary embodiments according to the present invention.

In certain exemplary embodiments according to the present invention the tubing adapter or components thereof are not adapted or cannot—during the intended use—change or manipulate the fluid flowing through it, for example by heating, in particular by aimed or intended heating.

In some exemplary embodiments according to the present invention neither the tubing adapter nor components thereof are placed within a bypass line for the pump.

In certain exemplary embodiments according to the present invention the dialysis fluid tubing system comprises no bypass line for the pump.

In some exemplary embodiments according to the present invention neither the tubing adapter nor its components are devices for limiting a pressure or do not act as such.

In certain exemplary embodiments according to the present invention the tubing adapter or its components are devices for ensuring a minimum pressure or act as such.

For example, in some exemplary embodiments according to the present invention the non-return valve or the pressure stop valve mentioned herein are not intended to limit a pressure by opening once a sufficiently high pressure has been reached. Rather, it closes once the pressure is too low.

In certain exemplary embodiments according to the present invention the dialysis fluid tubing system comprises a tubing section which is intended to be inserted into a pump, for example an occluding pump such as a roller pump.

In some exemplary embodiments according to the present invention, the tubing adapter, its locking mechanism or its device for generating or amending a flow resistance is a valve, a throttle and/or an aperture or comprises at least one of the latter elements.

In the case of a valve, it can be for example a non-return valve or a pressure stop valve having a defined or pre-determined opening pressure.

In certain exemplary embodiments according to the present invention, the opening pressure of the locking mechanism of the tubing adapter is 50 hPa (or mbar) at least and 350 hPa at most, or both.

In some exemplary embodiments according to the present invention the minimum pressure mentioned above is 5 hPa, or it is 5 hPa higher than a pressure which prevails downstream of the tubing adapter or the locking mechanism.

In certain exemplary embodiments according to the present invention the device for generating or amending a flow resistance effects an amendment such that during use of the tubing adapter according to the present invention a pressure difference of at least 5 hPa and/or 1000 hPa at most, preferably at least 50 hPa and/or 400 hPa at most, particularly preferably of at least 100 hPa and/or 350 hPa at most, prevails over the device or over the tubing adapter.

In some exemplary embodiments according to the present invention the dialysis fluid tubing system is integral with the tubing adapter or firmly connected to it. Firmly connected may mean that the connection can only be released in a destructive manner.

In certain exemplary embodiments according to the present invention the dialysis fluid tubing system further comprises a container or bag (for example a collecting or storage container) comprising dialysis fluid or is connected thereto. This fluid is intended for flowing through the tubing system. Also, the dialysis fluid tubing system may optionally comprise a pump or be connected with a pump arranged in a manner such that it can convey the dialysis fluid in the lumen of the tubing system. The pump can be embodied as a displacement pump, for example a roller pump.

Irrespective of its name as used herein, in some exemplary embodiments according to the present invention the dialysis fluid tubing system may be a tubing system for medical fluids other than dialysis fluid wherever this appears possible to the skilled person.

The container may be embodied as one or more bags. Such bags are described in U.S. Patent Application Publication No. 2005/020959, by way of example, the contents of which are expressly incorporated herein in its entirety by reference thereto.

In some exemplary embodiments according to the present invention the dialysis fluid tubing system comprises a heating device for heating the dialysis fluid or is interconnected with it or comprises a section which is intended to be interconnected with a heating device in use.

In certain exemplary embodiments according to the present invention, the heating device is arranged upstream to the tubing adapter.

The heating device may be one of those ones which require a constant, positive pressure within the interior of the container for achieving the desired heating results.

In some exemplary embodiments according to the present invention, the heating device is a bag heater.

In certain exemplary embodiments according to the present invention, the dialysis fluid tubing system is a disposable.

In some exemplary embodiments according to the present invention, the dialysis fluid tubing system is a dialysis fluid tubing.

In certain exemplary embodiments according to the present invention, the medical device is blood treatment device, for example a dialysis device, a filtration device, a diafiltration device or any other dialysis device known to the skilled person.

In some exemplary embodiments according to the present invention, the medical device is a treatment system or a treatment device having an extracorporeal blood circuit and/or a tubing set or system or is interconnected with one of these.

In certain exemplary embodiments according to the present invention, the medical device is a dialysis device, which is particularly configured to be used for continuous venovenous hemodiafiltration (CVV-HDF) or is configured for acute dialysis, or both.

In some exemplary embodiments according to the present invention, the tubing adapter is interconnected with the dialysis fluid tubing system downstream of a heating device, in particular downstream of a bag heater. The heating device is also interconnected with the dialysis fluid tubing system.

In certain exemplary embodiments according to the present invention, the tubing adapter is interconnected with the dialyzer coupling of the dialysis fluid tubing system. To this end, the tubing adapter according to the invention may be embodied to be interconnected with, for example, the one or several dialyzer couplings by plug connections, by plug-screw connections or the like, in particular without using tools or further connecting elements.

The term tubing "adapter" as used herein is not intended to be construed in a limiting manner such that the tubing adapter according to the present invention was intended to interconnect something that could not be interconnected with each other without the adapter. Rather, the term encompasses also an intermediate element or interconnecting element which is intended to interconnect two tubing sections of a tubing system or a tubing section with a dialyzer in fluid communication with each other, in particular in a direct manner.

In certain exemplary embodiments, the present invention is directed to a dialysis liquid tubing system with at least one tubing adapter for connection with at least another tubing section of the dialysis liquid tubing system, wherein the tubing adapter comprises at least one closing mechanism for closing its lumen which can be flown through and/or a device for creating or changing a flow resistance of the tubing adapter, tubing section or dialysis liquid tubing system, wherein the dialysis liquid tubing system additionally comprises at least one container with dialysis liquid which is provided for flowing through the tubing system, and one pump, arranged for conveying the dialysis liquid in the dialysis liquid tubing system, or are each connected thereto or intended for connecting, in which the dialysis liquid tubing system further comprises a heating device for heating the dialysis liquid or is connected thereto or has a section, intended for connection with a heating device during use, the heating device is arranged downstream of the pump during use, and the tubing adapter is arranged downstream of the heating device but upstream of the dialyser.

Some, several or all of the exemplary embodiments according to the present invention may provide for one, several or all of the advantages stated above or hereinafter.

A pump, for example an occluding pump (e.g., a roller pump), which is arranged downstream of the heating device would be an alternative arrangement. The function of the tubing adapter having, for example, a non-return valve or a pressure stop valve would then be at least partly assumed by the occluding pump which could avoid a vacuum or negative pressure between heating device and dialyzer by its occluding effect. An arrangement according to the present invention with a dialysis fluid tubing system in which the heating device, for example a bag heater, is provided downstream of the pump and in which the tubing adapter according to the present invention is provided downstream of the heating device provides for the following advantages compared with said alternative solution: A vacuum or negative pressure within the heating device may not only be caused by the dialyzer (see the description made with respect to FIG. 3: a high TMP inside the dialyzer may have several reasons) but also by the aspiration or suction of the occluding pump as it is known for roller pumps. The undesired effect of a vacuum or a negative pressure inside the heating device may also be caused by the aspiration or suction effect of the occluding pump that is arranged downstream of the heating device.

Further, errors in the balancing are avoided because the heating device and in particular the bag heater—although being considered as an additional volume storage—is normally not being taken into account in the balancing system. By the tubing adapter according to the present invention changes resulting from vacuum and a collapsing vessel of the heating device, in particular of the bag heater, as is the case with the alternative solution described above, may advantageously be avoided.

Further, by means of the present invention a warming of the dialysis fluid while the dialysis fluid is not being conveyed, as it may happen with an alternative arrangement, may be avoided with certain bicarbonate containing solutions. Such warming may deteriorate the quality of the dialysis fluid. This may result in precipitations of the dialysis fluid.

An undesired cooling of the dialysis fluid before the fluid enters the dialyzer may be advantageously avoided by the fact that according to the present invention the pump is located upstream of the heating device. An undesired cooling might result in deviations of the temperature which are difficult to estimate. According to the present invention such deviations may be avoided while accomplishing the advantages provided by the present invention.

For detecting a vacuum or a negative pressure inside the heating device, for example a bag heater, in order to avoid same, by means of the solution provided by the present invention or by the arrangement of the tubing adapter or its components between the heating device and the dialyzer in a manner according to the present invention, it is not required to monitor the filtrate pressure, i.e., the dialysate fluid pressure inside the dialyzer close to the membrane, or another pressure, with regard to a suitable minimum value. For example, there is essentially no relevant flow resistance between the filtrate pressure monitoring and the heating device in an arrangement for continuous veno-venous hemodiafiltration (CVV-HDF). Though it would be possible after a correction by a hydrostatic pressure difference to identify a minimum filtrate pressure at which the pressure inside the heating device is for sure sufficiently high to avoid collapsing of the bag, for example, the flow rate of the pump could be decreased if and when the pressure falls below the minimum filtrate pressure, however, to this end a control circuit would be required. This would mean costs and inconvenience, maintenance, calibration, and the like. According to the present invention, this is not necessary.

Also, such a solution bears the risk that false alarms might occur within the permitted range of flow rates of the pump and that certain treatment parameters are not admissible. Therefore uninterpretable warnings may occur (heating bag running dry, balance warnings, heater alerts). By using the tubing adapter according to the present invention the minimum filtrate pressure does not have to be monitored.

According to another advantage, the pressure inside the bag of the heating device may be increased by the tubing adapter according to the present invention by a required value ranging between 5 and 1000 hPa, preferably between 50 and 400 hPa, particularly preferably between 100 and 350 hPa. This value may be set or is selectable by a known device as mentioned above, such as a valve, based on the opening pressure in the flow direction.

Increasing the pressure in a manner possible according to the present invention advantageously counteracts or mainly avoids an undesired out-gassing of the solution when in contact with the warm heating surface, as it may happen at a low pressure. Hence, a pH shift caused by the out-gassing and in particularly by the out-gassing of $CO_2$ and, hence, undesired precipitations of calcium-carbonate and other chemical compounds from the flowing solution may be avoided.

According to another advantage of the tubing adapter according to the present invention the latter may be retrofitted once collapsing of the heating device or the heating bag is identified. In this way, a costly and complex integration of, for example, a non-return valve or a pressure stop valve into each of the manufactured dialysis fluid tubing systems may be avoided or waived.

Below, exemplary embodiments of the present invention are explained with reference to the accompanying drawings in which same or identical elements are referred to by identical reference numerals.

DETAILED DESCRIPTION

Figure 1:
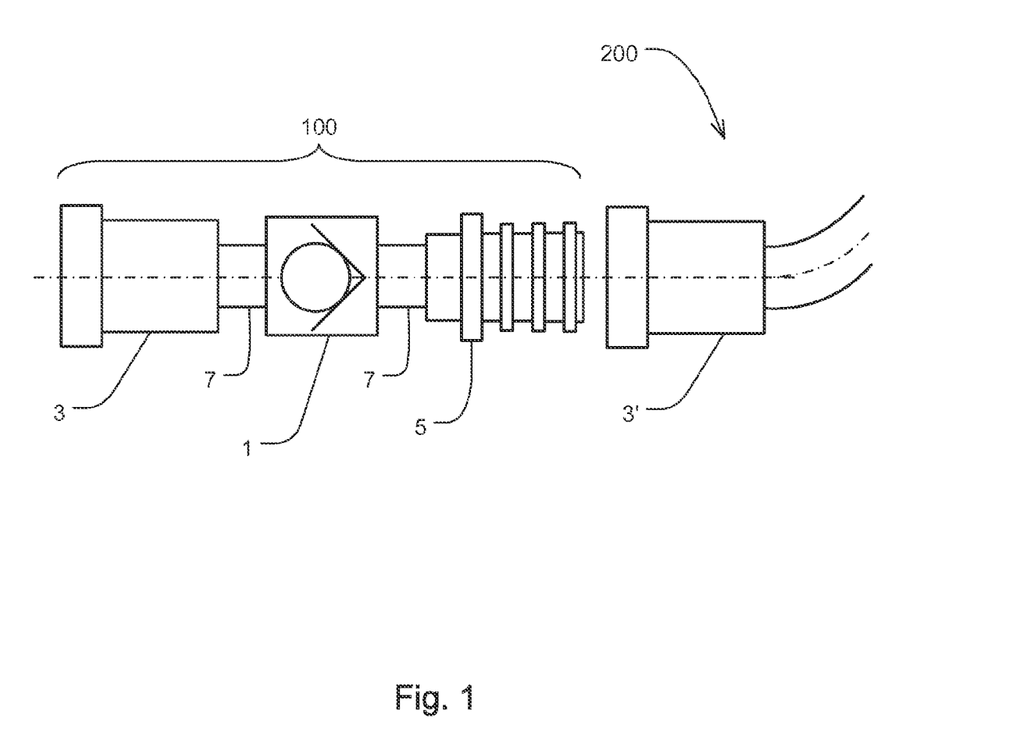
FIG. 1 shows schematically a tubing adapter according to the present invention having a non-return valve and two tubing connectors.
Figure 2:
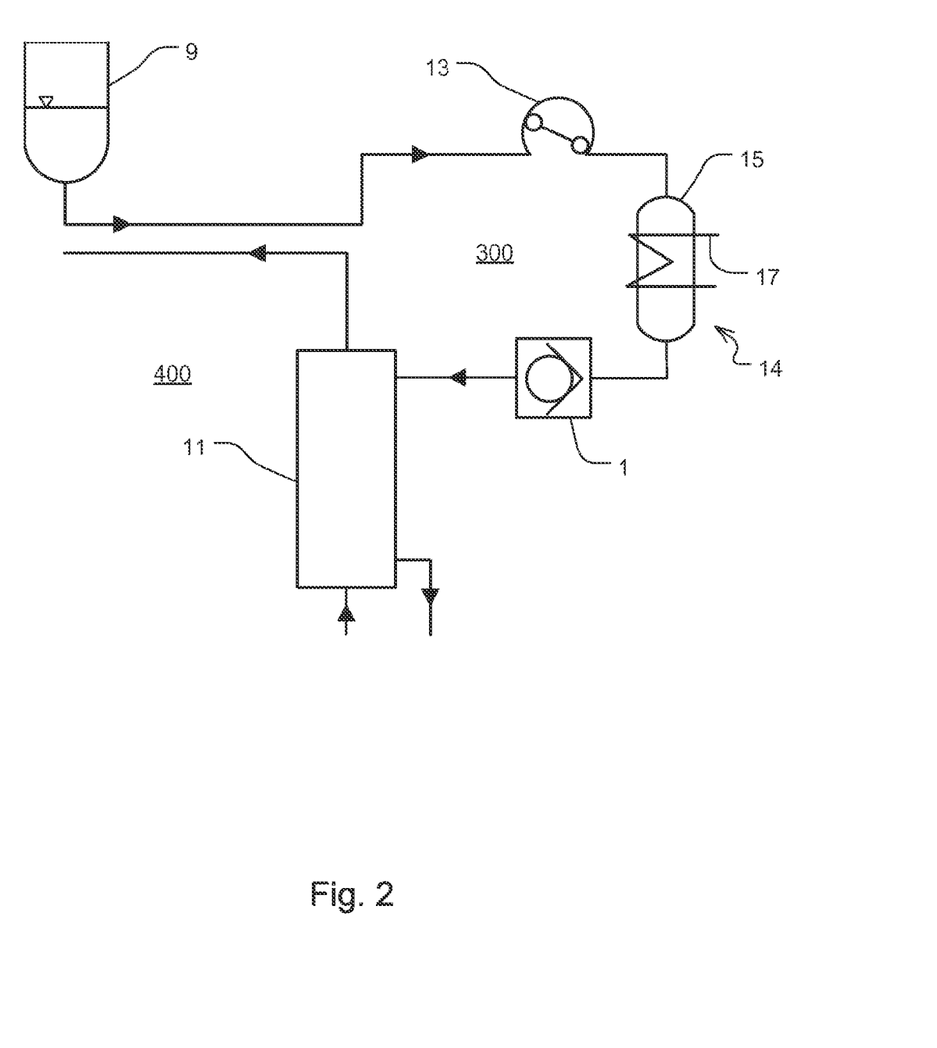
FIG. 2 shows schematically a dialysis fluid tubing system according to the present invention with an integrated non-return valve.
Figure 3:
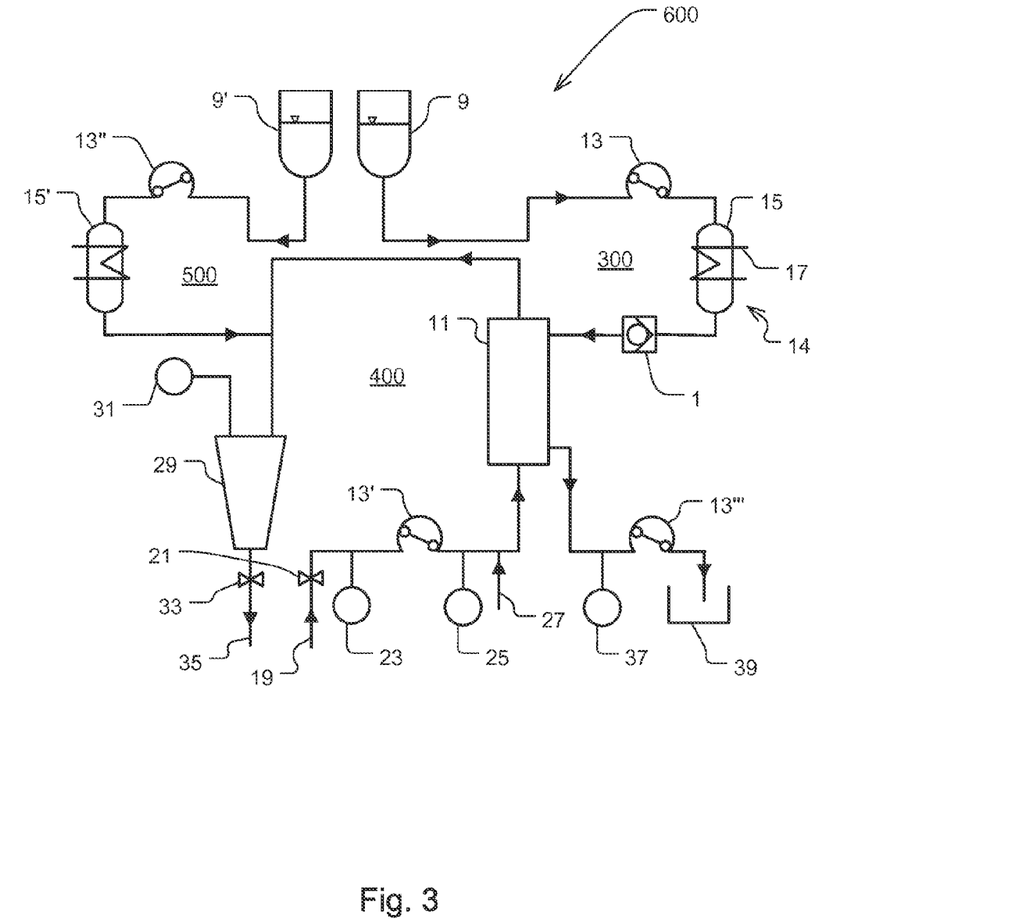
FIG. 3 shows schematically a medical device for dialysis according to the present invention with an extracorporeal blood circuit and a dialysis fluid tubing system according to the present invention.

FIG. 1 shows schematically a tubing adapter 100 according to the present invention, which in this exemplary embodiment is intended for being connected with a tubing section 200 of a dialysis fluid tubing system 300 (see FIGS. 2 and 3).

In this exemplary embodiment the tubing adapter 100 according to the present invention consists of a locking mechanism, which is embodied as a non-return valve 1 (below also referred to as valve 1) and which is illustrated as such, two tubing connectors 3, 5 and two optionally provided short tubing sections 7 of the tubing adapter 100. The tubing adapter 100 may comprise further components.

In this exemplary embodiment the particular components of the tubing adapter 100 are firmly connected to each other, for example by bonding or ultrasound welding. However, the components may be releasably interconnected to each other as well. This is advantageous because at the site of its use the tubing adapter 100 can still be provided with tubing connectors 3, 5 in various sizes which can be connected to corresponding tubing connectors of tubing systems other than the tubing system 300 which is shown here.

For connecting the tubing adapter 100, the tubing connectors 3, 5 are interconnected with tubing couplings of the dialysis fluid tubing system 300. Tubing connector 5 is embodied as a first coupling, here also referred to as "male" part or connector, and tubing connector 3 is referred to as "female" part or connector. In this exemplary embodiment, the female part of the coupling (tubing connector 3) is embodied identically to a corresponding tubing connector 3' of the known tubing section 200.

The two tubing connectors 3', 5 are assembled or plugged into each other such that the dialysis fluid tubing system 300 is extended hereby by the uncovered or free length of the tubing adapter 100.

With regard to FIG. 1, the dialysis fluid flows through the tubing adapter 100 from right to left during normal use of the tubing adapter. Valve 1 of tubing adapter 100 opens—for example against the force of a spring—if and when a minimum pressure prevails upstream of the valve 1, that is, on the right-hand side thereof with respect to FIG. 1.

With reference to FIGS. 2 and 3, it is explained in more detail how the tubing adapter 100 or its valves 1 work.

FIG. 2 shows the dialysis fluid tubing system 300 according to the present invention as part of a medical device 600 according to the present invention (see FIG. 3), which in this case or exemplary embodiment is a treatment system for dialysis. The medical device 600 further comprises an extracorporeal blood circuit 400 (shown as a section or cut here, see also FIG. 3), and also a dialyzer 11 which is being flown through by both fluids (blood and dialysis fluid) for exchange of substances.

The dialysis fluid tubing system 300 which can be embodied as a single use tubing system (disposable) is being filled with dialysis fluid from a bag 9. The dialysis fluid is conveyed along the dialysis fluid tubing system 300 by a pump 13, which, by way of example only, is embodied as a roller pump. The dialysis fluid from bag 9 may flow into a heating device 14 which is arranged downstream of pump 13, that is, on the pressure side of pump 13, by gravity or by aspiration of the pump, or both. The heating device 14 shown in the figures is—by way of example—embodied as a device comprising at least a heating bag 15 and heating rods or heating spindles 17, for which reason it is herein also called a bag heater. The dialysis fluid is heated inside the heating bag 15. For ensuring that heat is transferred from the heating device 14 or the heating spindles 17 to the heating bag 15 it is helpful or maybe even necessary that compared to the atmosphere a positive pressure of the dialysis fluid prevails inside the heating bag 15. In this way, the wall of heating bag 15 nestles or adjusts to the heating spindles 17, thereby enabling or promoting the heat transfer. In other words, by a positive inside pressure, collapsing of the heating bag 15 and a deterioration or interruption of the heat transfer is avoided.

The valve 1 is arranged further downstream of the pump 13 and downstream of the heating device 14. In this exemplary embodiment the valve 1 is also integrated into the tubing system 300. Therefore, FIG. 2 shows no tubing adapter 100 according to the present invention. Valve 1, being integrated as is shown here, therefore needs no tubing couplings such as are shown in FIG. 1. Alternatively, the valve 1 may be interconnected with a tubing system 300 as is shown in FIG. 1, the valve then being part of tubing adapter 100 according to the present invention.

Valve 1 is arranged within the tubing system 300 such that it closes if the pressure upstream of valve 1, that is, between valve 1 and heating device 14 or heating bag 15, is too low. By closing, it is avoided that a pressure which is too low and which prevails downstream of valve 1 propagates upstream of valve 1 and into the heating bag 15 and possibly results in a negative pressure (related to the atmosphere) or in an inside pressure that is lower than desired. As already discussed above, a positive pressure inside the heating bag 15 is helpful for establishing or securing the desired or expected heat transfer.

In certain exemplary embodiments according to the present invention, the opening pressure is between 5 and 1000 hPa, preferably between 50 and 400 hPa, particularly preferably between 100 and 350 hPa. That is, the inner pressure or inside pressure of the heating bag 15 must be at least as high as this value or must exceed a pressure downstream of the valve by at least this value for the valve 1 to open, if the flow loss occurring in the tubing section between the heating bag 15 and the valve 1 are not taken into account. In other words, the pressure upstream of valve 1 must be at least that high (between 5 am 1000 hPa, preferably between 50 and 400 hPa, particularly preferably between 100 and 350 hPa) or exceed by this value to overcome the opening pressure of valve 1.

A lower pressure downstream of valve 1, and, in consequence, evacuating or sucking dry of the dialysis fluid further upstream up to the heating bag 15, may in practice have several reasons. This will be explained in more detail with regard to FIG. 3 making reference to a complete treatment system.

FIG. 3 shows schematically a medical device 600 (also referred to as a treatment system) for dialysis, which in this exemplary embodiment according to the present invention is for the continuous veno-venous hemodiafiltration (a combination of hemofiltration and hemodialysis), also known as CVV-HDF, with an extracorporeal blood circuit 400, a substitute tubing system 500 and a dialysis fluid tubing system 300 according to the present invention.

Blood is taken from the patient by an arterial connector 19 or an arterial line of the extracorporeal blood circuit 400. A stop-cock 21 is arranged downstream of the arterial connector 19. Downstream of the latter, the arterial pressure is measured by a pressure sensor 23; further downstream there is a blood pump 13'. Between the blood pump 13' and the connector of the arterial line for connecting the arterial line with the dialyzer 11, the hemofiltration pressure is measured by a pressure sensor 25. Downstream of the pressure sensor 25, heparin is administered to the blood for anticoagulation at admission port 27.

Within the dialyzer 11, substances are exchanged with the dialysis fluid of tubing system 300 which leaves the dialyzer 11 as dialysate. This will be further explained below.

Downstream of the dialyzer 11, the blood flows in a venous drop chamber 29, in which the venous pressure is measured by a pressure sensor 31. A stop-cock 33 is arranged downstream thereof. The blood is returned into the vessels of the patient by a venous connector 35.

The substitute tubing system 500 serves to partly substitute the fluid volume which was removed by filtration within the dialyzer 11 during treatment. To this end, substituate fluid from a bag 9' is used. The substituate is conveyed within the substituate tubing system 500 by a substituate pump 13" into a heating bag 15' where it is heated before it is fed into the blood circuit 400.

The tubing system 300 upstream of the dialyzer 11 has already been explained with reference to FIG. 2. The filtrate pressure is measured downstream of the dialyzer 11 by a pressure sensor 37; further downstream, the dialysate is—together with the filtrate—conveyed into a collecting bag 39 by a pump 13', or disposed.

In the following, reasons for a low pressure downstream of valve 1 are discussed.

A lower pressure (when compared to the atmosphere) downstream of valve 1, which would possibly result in evacuating or sucking dry of the heating bag 15 if there was no valve 1, may be caused by, for example, deposit on the filter membrane of the dialyzer 11 (on the membrane side of the blood circuit 400, for example, by blood that starts clotting). This results in a decrease of the permeability of the filter membrane in the dialyzer and also to an increased transmembrane pressure TMP.

Regardless of this phenomenon, using filter membranes of low permeability may also result in this low pressure problem on the dialysis side of the dialyzer 11 (the same effect as with deposit on the membrane may occur here). Thus, a low permeability results in a high TMP for achieving a desired or requested exchange of substances in the dialyzer 11. When using filter membranes of low permeability, the tubing adapter 100 according to the present invention and/or the dialysis fluid tubing system 300 may, therefore, be used for avoiding a marked negative pressure and for ensuring an optimal, desired or expected heat transfer from the heating device housing to the heating bag 15.

A pressure on the dialysis side that is possibly too low for the needs of the heating bag occurs particularly during continuous veno-venous hemodiafiltration (CVV-HDF) dialysis treatments, which require high filtration flow rates and a correspondingly high pressure gradient over the filter membrane, i.e., a high transmembrane pressure TMP.

The pressure reference point for the area around the filter membrane of the dialyzer 11 is located in the area of the venous connector 35. The pressure reference point for the dialysis side is the pressure sensor 37. From there, the pressure of the dialysis side of the filter membrane (in the tubing system 300) may be tracked back by considering pressure differences caused by flow and by hydrostatic pressure differences. Accordingly, with a sufficiently high TMP, a pressure below atmosphere may prevail within the heating bag 15 and the heating bag may collapse if this is not avoided by, for example, using the tubing adapter 100 or the dialysis fluid tubing system 300 according to the present invention.

What is claimed is:

1. A dialysis fluid tubing system, comprising:
   a first tubing section configured to interconnect with a heating device or comprising a heating bag;

a pumping section configured to interconnect with a pump and arranged upstream of the first tubing section; and at least one of:
(a) at least one tubing adapter comprising at least one of:
(i) at least one locking mechanism for blocking a flow-through lumen; or
(ii) a device for generating or amending a flow resistance of the at least one tubing adapter or of a second tubing section of the dialysis fluid tubing system connected to the at least one tubing adapter,
wherein the at least one tubing adapter is configured to be arranged downstream of the first tubing section,
wherein the at least one locking mechanism or the device for generating or amending a flow resistance is configured to prevent a pre-defined pressure upstream of the at least one tubing adapter,
wherein the pre-defined pressure is a pressure below a pre-defined minimum pressure; and
wherein the pre-defined minimum pressure is a pressure at which the first tubing section or the heating bag does not collapse; or
(b) one tubing adapter integral with the dialysis fluid tubing system and comprising at least one of:
(i) at least one locking mechanism for blocking a flow-through lumen; or
(ii) a device for generating or amending a flow resistance of the one tubing adapter or of a second tubing section of the dialysis fluid tubing system connected to the one tubing adapter,
wherein the one tubing adapter is arranged downstream of the first tubing section,
wherein the at least one locking mechanism or the device for generating or amending a flow resistance is configured to prevent a pre-defined pressure prevailing upstream of the one tubing adapter,
wherein the pre-defined pressure is a pressure below a pre-defined minimum pressure, and
wherein the pre-defined minimum pressure is a pressure at which the first tubing section or the heating bag does not collapse.

2. The dialysis fluid tubing system according to claim 1, wherein the at least one tubing adapter or the one tubing adapter is or comprises at least one of a valve, a throttle or an aperture.

3. The dialysis fluid tubing system according to claim 1, wherein an opening pressure of the locking mechanism is between 5 hPa and 1000 hPa.

4. The dialysis fluid tubing system according to claim 1, wherein an opening pressure of the locking mechanism is between 50 hPa and 400 hPa.

5. The dialysis fluid tubing system according to claim 1, wherein an opening pressure of the locking mechanism is between 100 hPa and 350 hPa.

6. The dialysis fluid tubing system according to claim 1, wherein at least one of:
the device for generating or amending the flow resistance of the at least one tubing adapter effects an amendment such that during use a pressure difference of between 5 hPa and 1000 hPa prevails over the device or over the at least one tubing adapter; or
the device for generating or amending the flow resistance of the one tubing adapter effects an amendment such that during use a pressure difference of between 5 hPa and 1000 hPa prevails over the device or over the one tubing adapter.

7. The dialysis fluid tubing system according to claim 1, wherein at least one of:
the device for generating or amending the flow resistance of the at least one tubing adapter effects an amendment such that during use a pressure difference of between 50 hPa and 400 hPa prevails over the device or over the at least one tubing adapter; or
the device for generating or amending the flow resistance of the one tubing adapter effects an amendment such that during use a pressure difference of between 50 hPa and 400 hPa prevails over the device or over the one tubing adapter.

8. The dialysis fluid tubing system according to claim 1, wherein at least one of:
the device for generating or amending the flow resistance of the at least one tubing adapter effects an amendment such that during use a pressure difference of between 100 hPa and 350 hPa prevails over the device or over the at least one tubing adapter; or
the device for generating or amending the flow resistance of the one tubing adapter effects an amendment such that during use a pressure difference of between 100 hPa and 350 hPa prevails over the device or over the one tubing adapter.

9. The dialysis fluid tubing system according to claim 1, wherein the at least one tubing adapter is integral with the dialysis fluid tubing system.

10. The dialysis fluid tubing system according to claim 1, further comprising:
at least one bag with dialysis fluid intended for flowing through the dialysis fluid tubing system; and
the pump, wherein the pump is arranged for conveying the dialysis fluid in the dialysis fluid tubing system,
wherein the at least one bag or the pump is connected to or intended for connection with the dialysis fluid tubing system.

11. The dialysis fluid tubing system according to claim 1, wherein the heating device or the heating bag is configured to heat dialysis fluid.

12. The dialysis fluid tubing system according to claim 11, wherein the heating device is configured to interconnect with the first tubing section or the heating bag.

13. A medical device for use with the at least one dialysis fluid tubing system according to claim 1.

14. The medical device according to claim 13, wherein the medical device is a blood treatment device or a dialysis device.

15. The dialysis fluid tubing system according to claim 1, wherein the first tubing section comprises the heating bag.

16. The dialysis fluid tubing system according to claim 1, wherein an opening pressure of the at least one locking mechanism is selected such that at least one of the container comprising dialysis fluid or the heating bag does not collapse.

17. A method of using the dialysis fluid tubing system according to claim 1, the method comprising:
interconnecting the at least one tubing adapter with the dialysis fluid tubing system in fluid communication.

18. The method according to claim 17, wherein the at least one tubing adapter is interconnected with the dialysis fluid tubing system downstream of the heating device or the heating bag.

19. The method according to claim 17, further comprising:

interconnecting the at least one tubing adapter with dialyser couplings of the dialysis fluid tubing system.

\* \* \* \* \*